United States Patent [19]

Candau et al.

[11] Patent Number: 5,247,828
[45] Date of Patent: Sep. 28, 1993

[54] PROCEDURE AND DEVICE FOR MEASUREMENT OF THE GELLING OF PARAFFINIC PETROLEUM PRODUCTS, ESPECIALLY CRUDE PRODUCTS

[75] Inventors: Sauveur P. Candau, Strasbourg; Pierre Lemarechal, Obernai; Yves Thiriet, Strasbourg; Claude Schranz, Ville d'Avray; Bernard Pesneau, le Val St. Germain, all of France

[73] Assignee: Total Compagnie Francaise des Petroles, Paris, France

[21] Appl. No.: 834,522

[22] PCT Filed: Jun. 26, 1990

[86] PCT No.: PCT/FR90/00472
§ 371 Date: Feb. 7, 1992
§ 102(e) Date: Feb. 7, 1992

[87] PCT Pub. No.: WO91/00516
PCT Pub. Date: Jan. 10, 1991

[30] Foreign Application Priority Data

Jul. 3, 1989 [FR] France .................. 89 08888

[51] Int. Cl.⁵ .............................. G01N 33/26
[52] U.S. Cl. ................................. 73/64.42
[58] Field of Search ............ 73/64.42, 64.41, 53.01, 73/53.07, 597

[56] References Cited

U.S. PATENT DOCUMENTS 3,040,562  6/1962  Fitzgerald et al. ............. 73/53.02
3,413,595 11/1968 Babikov ...................... 73/597 X
3,952,578  4/1976 Jacobs ........................ 73/64.42
4,327,587  5/1982 Docekal et al. ................ 73/597 X
4,785,287 11/1988 Honma et al. ................ 73/53.07 X
4,933,911  6/1990 Sondergeld et al. ............. 73/597 X

FOREIGN PATENT DOCUMENTS 279839 12/1991 Japan ........................ 73/64.41
968561  9/1964 United Kingdom ............ 73/53.02

Primary Examiner—Hezron E. Williams
Assistant Examiner—Joseph W. Roskos
Attorney, Agent, or Firm—Sughrue, Mion, Zinn Macpeak & Seas

[57] ABSTRACT

The invention relates to a process and a device for measuring the gelling of paraffin petroleum products, in particular, crude oil. The process involves: measuring, with respect to the temperature and over a given thickness, the propagation velocity and the amplitude of an ultrasonic wave in the crude oil being analysed; then determining the transition temperature $T_t$, at which a sudden change in the thermal variation in the inverse of the propagation velocity is observed; determining the ratio of the slopes for the propagation velocity inverse obtained between the linear parts of the thermal variation of said propagation velocity, around said brake point corresponding to $T_t$, above and below, respectively, the determined temperature $T_t$; determining the ultrasonic signal amplitude difference $\Delta A$ between the temperature $T_t$ and a given lower reference temperature, for example $T_t - 5°$ C.

22 Claims, 3 Drawing Sheets

PROCEDURE AND DEVICE FOR MEASUREMENT OF THE GELLING OF PARAFFINIC PETROLEUM PRODUCTS, ESPECIALLY CRUDE PRODUCTS

BACKGROUND OF THE INVENTION

The Patent Abstract of Japan, Vol. 6, No. 116 (P-125) (994), Jun. 29, 1982, 8 JP-A-57 44 852, Mar. 13, 1982 discloses a method and an apparatus for revealing the solid state of an intentionally-congealed fluid in the pipe of a nuclear reactor. This process is not adapted for measurement of petroleum products.

The present invention concerns a procedure and device for measurement of the gelling of paraffinic petroleum products, especially crude products.

It is known that paraffinic crudes can form gels at temperatures approaching, or less than, 40° C. This gelling phenomenon, when it occurs during production or transport, may lead to problems involving the re-start-up of facilities. It is thus critically important to have available a method making it possible to determine what crudes are capable of gelling within a given temperature range and, as needed, to determine the minimum quantities of gelling-inhibitor or doping product needed to prevent the formation of gel.

Current conventional practice can measure the pour point of crudes (see Standard ASTM D-97 or AFNOR T60-103), this method consisting in cooling crude under determinate conditions in a special test tube equipped with a thermometer, and in looking to see whether, at each three-degree interval, the surface has or has not congealed. The temperature at which the surface of the crude congeals is the pour point.

It is also known how to measure, by differential caloric analysis, the incipient crystallization temperature of the crude, this latter corresponding, in fact, to a detectable exothermic phenomenon.

It is further known how to measure the rheological behavior of crudes, the flow properties of these latter ceasing newtonian behavior below a certain temperature, when paraffin crystals form within them.

However, none of these data, i.e., the measurement of the pour point, measurement of the incipient crystallization temperature, and the temperature at which rheological behavior changes, make it possible to know with certainty that operating difficulties will not occur in the event the crude is cooled below that temperature.

SUMMARY OF THE INVENTION

The present application attempts to meet this need for more reliable knowledge concerning gelling of paraffinic crudes during use and proposes a procedure for measurement of gelling of paraffinic crudes which is characterized mainly by the fact that, to determine if a crude is about to form a gel capable of hindering its use at a given temperature, this procedure comprises the following steps:

measuring, as a function of temperature and on a given thickness, the speed of propagation and the amplitude of an ultrasonic wave in the crude analyzed, then determining the transition temperature $T_t$ at which an abrupt change in the thermal variation of the reciprocal of the propagation speed is observed;

determining the value of the ratio of the slopes p of the reciprocal of the rate of propagation obtained between the linear portions of the thermal variation of this latter around said break point corresponding to $T_t$, below and above, respectively, the determined temperature $T_t$, and determining the difference $\Delta A$ of the amplitude of the ultrasonic signal between said temperature $T_t$ and a lower reference temperature equal, for example, to $T_t - 5°$ C., a significant break of slope (p > 1) at said temperature T and a high value of the difference A (A > 0.3 dB/cm at $T_t - 5°$ C.) signifying that gelling of the crude will very probably occur at temperatures below $T_t$, but that, to the contrary, gelling is not very likely for a slight variation of one of these parameters.

Applicant has found that knowledge of p and $\Delta A$ characterizes the physical state of crude paraffinic products. The gelling state of a crude implies, for the temperature below $T_t$ previously specified, the change of said thermal slope as well as a significant attenuation of the wave transmitted. Inversely, for crudes exhibiting no risks of gelling, at least one of these parameters remains more or less unchanged when the temperature $T_t$ is reached.

The invention also concerns a device for measurement of the rate of propagation and the amplitude of the ultrasonic wave. Any conventional device is suitable within the scope of the invention. The range of practical frequencies used lies between 300 KHz and 10 MHz. For example, use may be made of a device which measures the time of travel, or "flight time" and the amplitude of an ultrasonic signal which is propagated at a frequency of approximately 600 kHz through a thickness of crude of approximately 1 cm.

BRIEF DESCRIPTION OF THE DRAWINGS

Embodiments of the invention will now be described with reference to the attached drawings, in which.

DETAILED DESCRIPTION OF THE INVENTION

Figure 1:
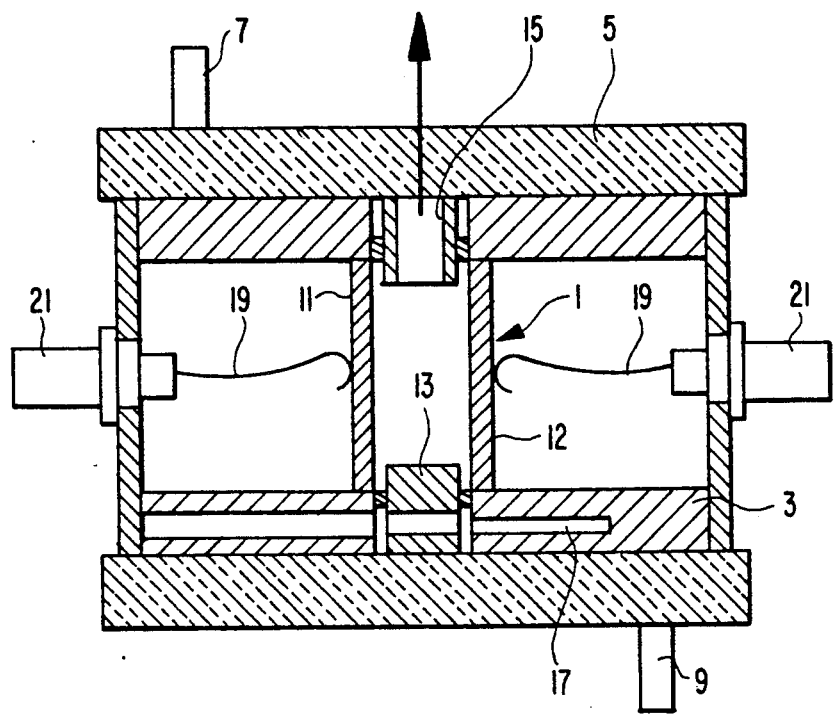
FIG. 1 is a schematic transverse cross-section of a measuring cell belonging to the invention device.

With reference to FIG. 1, the measuring apparatus according to the invention essentially comprises a central inner chamber 1 which holds the crude paraffinic product to be analyzed, this chamber being attached to a metal jacket 3 equipped with a thermostat covered with a thermal-insulation wall 5. The jacket 3 is kept thermostated by a water circuit which enters through an inlet orifice 7 and exists through an outlet orifice 9. The inner chamber 1 is cylindrical, its internal volume being delimited laterally by two disks 11 and 12 made of piezoelectric ceramic and which form transducer elements, i.e., an ultrasonic transmitter and receiver, respectively, belonging the apparatus, and by a ring-shaped part 13 attached to the jacket 3. In a special embodiment, the distance between the disks 11 and 12 is 14 mm, and the internal diameter of the chamber 1 is 26 mm. Consequently, the chamber volume is 7.5 cm³. The upper section of the ring-shaped part has a radial filling orifice 15 having a volume of approximately 0.5 cm³. The total product volume contained in the chamber is thus 8 cm³, the overflow of the orifice compensating for the withdrawal of the fluid contained in the chamber during cooling. A thermal probe 17, inserted in the thickness of the lower section of the ring-shaped part 13, makes it possible to raise the temperature of the product to be analyzed. The outer insulating wall 5 imparts to the entire assembly a thermal stability of several one-hundredths of a degree. The transducer components 11 and 12 are connected to the electronic measuring circuit by spring wires 19 in contact with the piezoelectric disks and by means of connector plugs 21.

Figure 2:
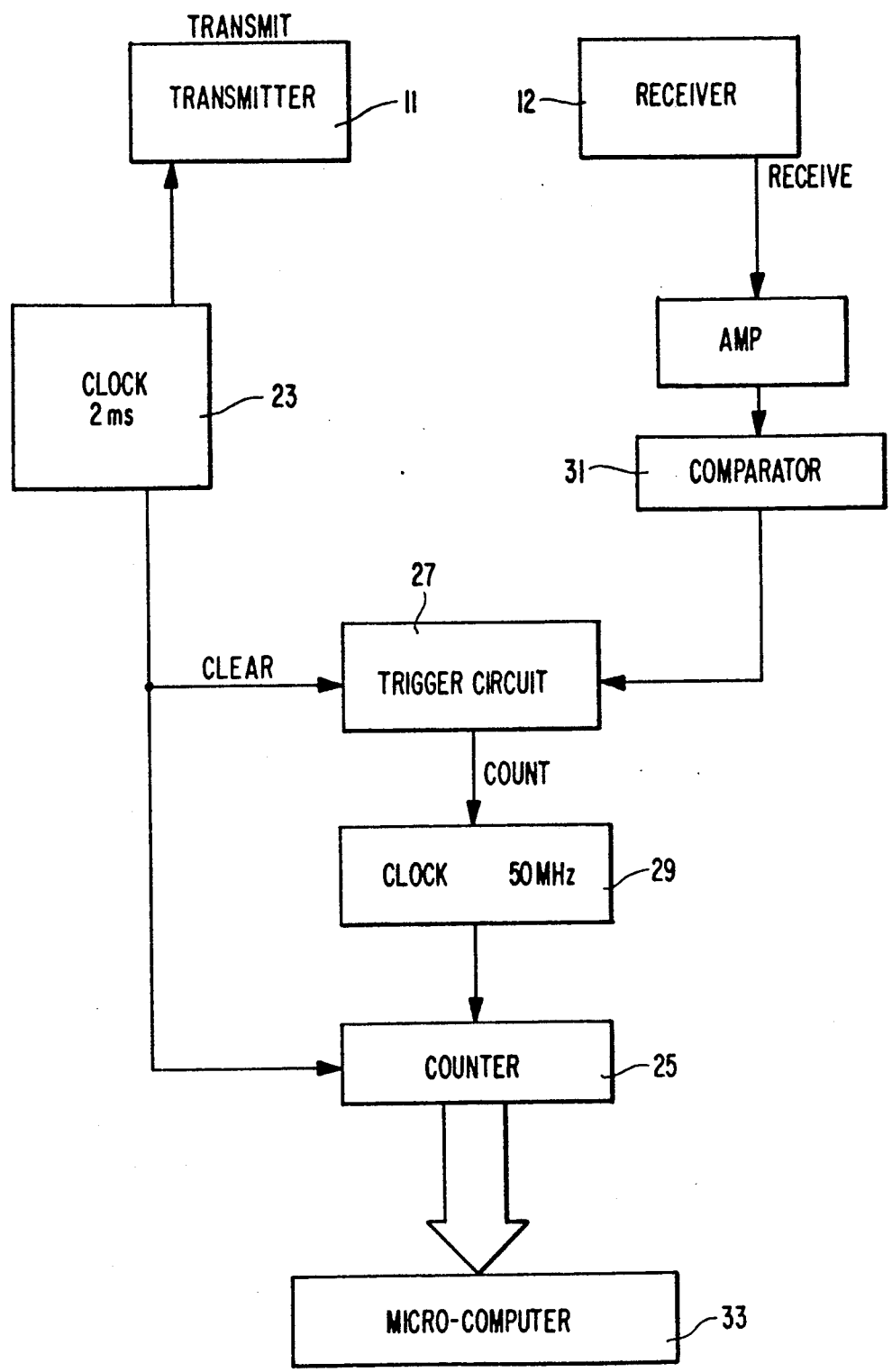
FIG. 2 represents the block diagram of the electronic circuit of this device.

FIG. 2 illustrates the diagram of the electronic circuit making it possible to measure the time of propagation, or flight time, of the ultrasonic wave in the fluid to be analyzed in the inner chamber of the apparatus. The principle underlying the processing of the signal as performed by this circuit is as follows:

Every two ms, a low-frequency clock 23 triggers the firing of an ultrasonic impulse transmitted by the transmitter transducer disk 11; simultaneously, a CLEAR signal at the clock outlet, having a duration of $\zeta_o$, is sent to the zero-reset input of a binary counter 25. This signal inhibits the functioning of the counter at a starting value. Another effect of the CLEAR signal is to actuate a trigger circuit 27 which generates a COUNT validation signal, authorizing the activation of impulses from a high-frequency clock 29 (50 MHz) whose function is to increase the counter 25 incrementally. This latter begins to count only at the end of the CLEAR signal, and thus after $\zeta_o$.

During this interval, the ultrasonic wave is propagated in the measuring cell, before reaching the receiver-transducer 12, which supplies an electric RECEIVE signal reflecting the ultrasonic energy received after passing through the crude. The RECEIVE signal, suitably amplified, triggers a comparator 31, which deactivates the COUNT trigger circuit 27; at this instant, the counter 25 stops. The duration of the COUNT signal equals the time of propagation of the ultrasonic wave in the crude. The digital indication of the counter corresponds to the value $\zeta - \zeta_o$, $\zeta_o$ acting only as a starting value making it possible to make the measurement values conform to the permitted measurement scale.

The digital counter outlets thus indicate a number equal to the difference between the durations of the COUNT and CLEAR signals, multiplied by the clock frequency. This number is transmitted to a computation unit 33 which computes an average value.

The measured propagation times of the ultrasonic wave are approximately 10 μs (approximately 14 mm at 1400 m/s). The variations of speed in the cell over the range of temperatures as a function of the crude are from 10 to 20%, and indicate variations of flight time of from 1 to 2 μs, i.e., 50 to 100 beats of the clock. One need only adjust the duration of the CLEAR signal as a function of this variation to adjust the reading properly within the measurement scale of the counter.

The resolution in time allowed by the clock is 20 ns. The various instabilities of the electronics introduce interference of several ns. To provide satisfactory precision, the computation unit computes the average of 1,000 acquisitions, thus reducing parasitic noise by a factor of approximately 30. The precision thus obtained is approximately 1 ns, or 1/10,000 of the time of propagation.

The ultrasonic attenuation of the propagation wave in the crude is measured based on the variation of amplitude of the signal received, after the thermal variations of the coupling of the transducer disks with the medium studied have been taken into account.

Figure 3:
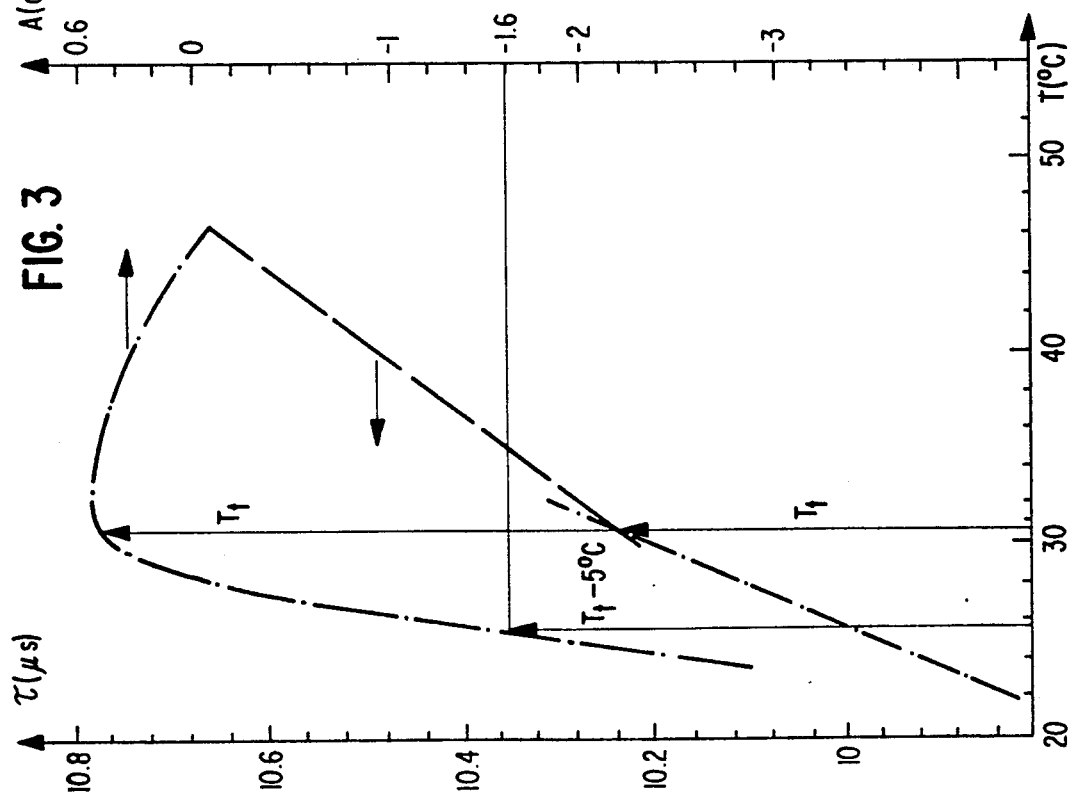
FIG. 3 is a diagram representing, as a function of temperature, the variation of time of propagation, or "flight time," (homogeneous with the reciprocal of the rate of propagation) and of the amplitude in dB of the ultrasonic wave in the crude.

FIG. 3 is a graphic representation of the variations of the propagation time and of the ultrasonic attenuation of a typical crude, i.e., no. 2 crude. This crude has a transition temperature below which it is capable of gelling, which is observed at the break point of the propagation-time curve at a value approaching 30° C. On either side of this point, the variations of propagation time are linear, the segment corresponding to $T < T_t$ having a more pronounced slope than that corresponding to $T > T_t$. The above-mentioned ratio p of the slopes for these segments is thus clearly superior to 1.

As regards ultrasonic attenuation corresponding to variations of the amplitude of the signal for which the dB scale is represented on the right, a rapid decrease in amplitude resulting from increased losses and corresponding to gelling of the crude is observed below a temperature approximating $T_t$. It will thus be seen that the parameters p and A cited are correlated with the physical state of the crude.

Figure 4:
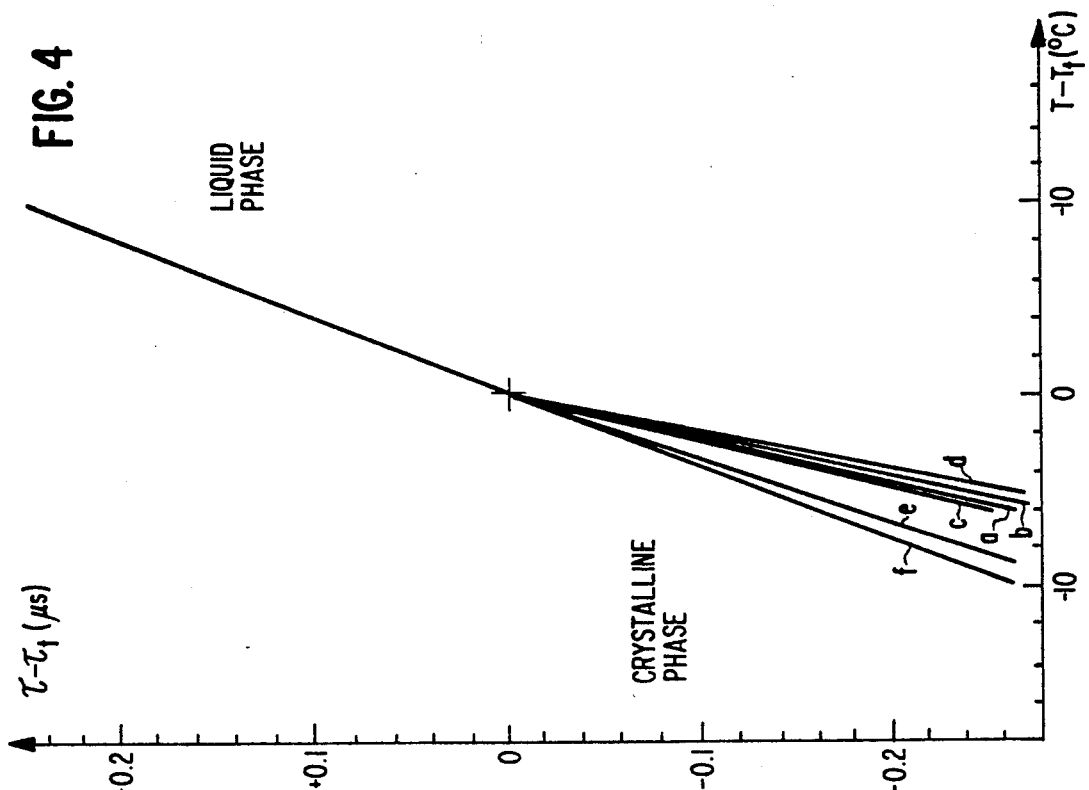
FIG. 4 is a graphic representation, expressed in reduced values $T-T_t$ and $\zeta - \tau \zeta$ (where $\zeta_t$ is the value of the time of travel at $T_t$) of the variations of the "flight time" of the ultrasonic wave as a function of temperature, for various paraffinic crudes.

FIG. 4 represents the variations of the propagation time (inversely proportional to the speed of propagation) as a function of temperature of the paraffinic crudes No.1:a, no.2: b, no. 3:c, no. 4:d, no. 5:e, and no. 6:f. It is found that the variations of propagation time as a function of temperature of all of these crudes are linear for $T < T_t$, with different slopes depending on the crudes. They are also linear for $T > T_t$ (liquid phase), but, in that case, they are also identical.

Crudes nos. 1, 2, 3, and 4 are characterized by a break of the slope at a characteristic temperature $T_t$ and by a variation, once again linear, but of slope p, which is greater when $T < T_t$ (crystalline phase).

For crude no. 5, the break of slope is only slightly pronounced (p≈1), while for crude no. 6, it is not detectable. These two latter crudes do not, in practice, pose risks of obstructing pipes under operating conditions. This shows clearly that p is one of the parameters characterizing the formation of gel, and that, if it is approximately equal to 1, there is very little chance that a gel will form.

Table I below recapitulates the values of p and the difference ΔA between $T_t$ and $T_t - 5°$ C., respectively, for the crudes mentioned.

TABLE I

| Crude | $T_t$ (°C.) | p | A (dB) |
|---|---|---|---|
| Crude no. 1 | 37.5 | 1.6 | 0.5 |
| Crude no. 2 | 31 | 1.8 | 2.1 |
| Crude no. 3 | 36 | 1.5 | 1.0 |
| Crude no. 4 | 36 | 1.9 | 2.3 |
| Crude no. 5 | 22 | 1.1 | 0 |
| Crude no. 6 | — | 1.0 | 0 |
| no. 2 + 200 ppm | 31 | 1.4 | 0 |
| no. 2 + 400 ppm | 31 | 1.4 | 0 |

In the cases of crude nos. 5 and 6, the difference ΔA remains close to zero, thereby confirming the information obtained by p.

The Table II below summarizes the test results for the different crudes studied and for doped crudes, and, in particular, two specimens of no. 2 crude doped with 200 and 400 ppm, respectively, a gelling-point depressing product.

TABLE II

| Crudes | Remarks | Test Result |
|---|---|---|
| Crude no. 6 | No transition Slight variation of A | No gelling possible within the temperature range studied |
| Crude no. 5 | $p \simeq 1$   $A \simeq 0$ | |
| Crude no. 1 | Pronounced transition | Gelling possible when $T < T_t$ |
| Crude no. 2 | Strong variation of A | |
| Crude no. 4 | $p > 1$ | |
| Crude no. 3 | $\Delta A$ high when $T <_t$ | |
| Crude no. 2 + doping agent | Marked transition Slight variation of A $p > 1$   $A \simeq 0$ | No gelling possible within the range of temperature studied |

The presence of the doping agent is characterized by the presence of attenuation ($\Delta A \simeq 0$) of the ultrasonic propagation wave.

Consequently, the method proves to be valid also for doped crudes for which gelling can be prevented by adjusting the quantities of the doping product until a value of $\Delta A$ of approximately zero is obtained.

This method could be applied to other materials besides paraffinic crudes, and, for example, to paraffinic petroleum cuts, and, in general, to petroleum-derived products such as natural gas containing condensate (natural gas hydrates which one wants to prevent from being deposited within ducts, in particular by adding specific inhibitors); some products inherent in hydrocarbons, e.g., asphaltenes whose precipitation one wishes to prevent in these ducts; paraffins; waxes, etc. Furthermore, in the example described, the procedure was carried out in the absence of any particular pressure condition, the investigation being performed under atmospheric pressure. However, the scope of the principle underlying the invention also encompasses variation of this parameter, particularly for the study of ways to prevent the above-mentioned deposits. In this case, the measurement cell is pressurized using suitable conventional means.

We claim:

1. A process for measuring a gelling characteristic of a paraffinic crude, in order to determine a temperature at which said crude enters a gel state, said process including the steps of:
   introducing a sample of said crude into a chamber having a transmitter on a first side and a receiver on a second side thereof,
   transmitting ultrasonic waves between said transmitter and receiver, and through said crude while adjusting a temperature of said crude between transmissions of said ultrasonic waves,
   measuring a propagation speed of each of said ultrasonic waves through said crude, in order to obtain propagation rates of said ultrasonic waves with respect to temperature changes of said crude,
   determining a transition temperature at which said propagation rate abruptly changes, wherein said ultrasonic waves exhibit a first propagation rate when a temperature of said crude is below said transition temperature and said ultrasonic waves exhibit a second propagation rate when a temperature of said crude is above said transition temperature, and
   determining a ratio between reciprocals of said first and second propagation rates, in order to determine a probability that said crude will enter a gel state when cooled to said transition temperature.

2. A process according to claim 1, wherein a frequency of the ultrasonic wave propagating through said crude is between 300 kHz and 10 MHz.

3. A process according to claim 1, wherein a frequency of the ultrasonic wave propagating through said crude is 600 kHz and a distance of propagation of the ultrasonic wave in the crude is 1 cm.

4. A process according to claim 1, wherein a probability exists that said crude will enter said gel state when said ratio is substantially equal to unity.

5. A process according to claim 1, further comprising the steps of:
   measuring an amplitude of each of said ultrasonic waves received at said receiver,
   determining a difference between an amplitude of an ultrasonic wave measured at said receiver, when a temperature of said crude equals said transition temperature, and an amplitude of an ultrasonic wave measured at said receiver, when a temperature of said crude equals a reference temperature below said transition temperature,
   determining a likelihood that said crude will center said gel state based on a magnitude of said difference, wherein a likelihood that said crude will enter said gel state increases as said difference increases.

6. A process according to claim 5, wherein a strong likelihood exists that said crude will enter said gel state when said ratio is greater than unity and said difference has a large magnitude.

7. A process according to claim 1, further comprising the step of doping said paraffinic crude in order to prevent gelling, wherein a quantity of a doping product added to said crude is adjusted until an attenuation value of said crude approximately equals 0.

8. A process according to claim 1, wherein said crude constitutes a petroleum-derived product.

9. A process according to claim 8, wherein said petroleum-derived product constitutes natural gas.

10. An apparatus for measuring a gelling characteristic of a paraffinic crude, in order to determine a temperature at which said crude enters a gel state, said apparatus comprising:
    an inner chamber for holding said crude while measuring said gelling characteristic, said inner chamber being attached to a metal thermostated jacket, which is covered by a thermal insulation wall;
    two ultrasonic transducer disks forming a transmitter and a receiver, respectively, arranged in facing relation to one another and on opposite sides of said inner chamber, said two ultrasonic transducer disks forming lateral walls of said inner chamber; an
    circuit means, connected to said two ultrasonic transducer disks, for producing ultrasonic waves which propagate through said crude and for determining said gelling characteristics based on said ultrasonic waves.

11. An apparatus according to claim 10, wherein the two transducer disks are made of a piezoelectric ceramic.

12. An apparatus according to claim 10 wherein a distance between said two transducer disks is 14 mm.

13. An apparatus according to claim 10, wherein the two transducer disks are connected externally to outer spring wires connected to an electronic circuit, in said circuit means, which measures a time and amplitude of propagation of the ultrasonic wave propagated within the inner chamber.

14. An apparatus according to claim 10, further comprising:
    a computation unit for computing an average value of said slopes and said amplitude for a large number of ultrasonic waves in order to obtain an accuracy of approximately 1/10,000th of a time of travel of said ultrasonic wave through said crude, ultrasonic attenuation being further determined based on thermal variations of a coupling of the two transducers with the crude.

15. An apparatus according to claim 10, wherein the inner chamber is pressurized.

16. An apparatus according to claim 10, said circuit means further comprising:
    means for measuring a propagation speed of said ultrasonic waves through said crude and means for measuring, at said receiver, an amplitude of said ultrasonic waves.

17. An apparatus according to claim 10, wherein said inner chamber further comprises a thermal probe inserted in a thickness of a lower section of a ring shaped part surrounding said inner chamber, said thermal probe changing a temperature of said inner chamber and said crude therein.

18. An apparatus according to claim 10, wherein said electronic circuit further comprises:
    a low frequency clock for triggering transmission of each of said ultrasonic waves from said transmitter,
    a binary counter, connected to said clock, for counting, wherein said clock supplies a clear signal to said binary computer to inhibit a start of a counting function, and
    means for determining a propagation speed of said ultrasonic waves through said crude based on a count from said binary counter.

19. An apparatus according to claim 18, wherein said circuit means further comprises a trigger circuit, connected to said clock, for generating a count validation signal,
    a second clock for incrementing said binary counter, said count validation signal authorizing the activation of impulses from said second clock to said binary counter.

20. An apparatus according to claim 10, wherein said circuit means further comprises:
    a binary counter for counting a time between transmission of an ultrasonic wave and reception of said ultrasonic wave at the receiver, and
    means for supplying a clear signal to said counter to delay a start of a counting function a predetermined time period after transmission of an ultrasonic wave.

21. A process for measuring a gelling characteristic of a paraffinic crude, in order to determine a temperature at which said petroleum-derived product enters a gel state, said process including the steps of:
    introducing a sample of said petroleum-derived product into a chamber having a transmitter on a first side and a receiver on a second side thereof,
    transmitting ultrasonic waves between said transmitter and receiver, and through said petroleum-derived product while adjusting a temperature of said petroleum-derived product between transmissions of said ultrasonic waves,
    measuring a propagation speed of each of said ultrasonic waves through said petroleum-derived product, in order to obtain propagation rates of said ultrasonic waves with respect to temperature changes of said petroleum-derived product, determining a transition temperature at which said propagation rate abruptly changes, wherein said ultrasonic wave exhibits a first propagation rate when a temperature of said petroleum-derived product is below said transition temperature and said ultrasonic waves exhibit a second propagation rate when a temperature of said crude is above said transition temperature, and
    determining a ratio between reciprocals of said first and second propagation rates, in order to determine a probability that said petroleum-derived product will enter a gel state when cooled to said transition temperature.

22. A process according to claim 21, wherein said petroleum-derived product constitutes natural gas.

* * * * *